United States Patent [19]

Penny, III et al.

[11] Patent Number: 4,816,029
[45] Date of Patent: Mar. 28, 1989

[54] STENT FOR AORTIC HEART VALVE

[75] Inventors: William H. Penny, III, Santa Ana; Jonathan J. Rosen, Fountain Valley; George M. Acosta, Long Beach, all of Calif.

[73] Assignee: Medtronic, Inc., Minneapolis, Minn.

[21] Appl. No.: 261,393

[22] Filed: May 7, 1981

[51] Int. Cl.⁴ ............................................. A61F 2/24
[52] U.S. Cl. ........................................ 623/2; 623/900
[58] Field of Search .................... 3/1.5, 1; 623/2, 900

[56] References Cited

U.S. PATENT DOCUMENTS

| | | | |
|---|---|---|---|
| 3,570,014 | 3/1971 | Hancock | 3/1.5 |
| 3,755,823 | 9/1973 | Hancock | 3/1.5 |
| 3,983,581 | 10/1976 | Angell et al. | 3/1.5 |
| 4,035,849 | 7/1977 | Angell et al. | 3/1.5 |
| 4,084,268 | 4/1978 | Ionescu et al. | 3/1.5 |
| 4,106,129 | 8/1978 | Carpentier et al. | 3/1.5 |
| 4,172,295 | 10/1979 | Batten | 3/1.5 |
| 4,222,126 | 9/1979 | Boretos et al. | 3/1.5 |

Primary Examiner—Ronald L. Frinks
Attorney, Agent, or Firm—Joseph F. Breimayer; John L. Rooney; Robert J. Klepinski

[57] ABSTRACT

A plastic stent for a prosthetic trileaflet heart valve consisting of a cylindrical body portion terminating at one end in three apical, spaced commissure posts, and at the other end, in a skirt comprising three arcuate extensions, each extension being provided with an interrupted channel adjacent the outer edge thereof. An optional metal ring may be mounted over the skirt adjacent the body portion. A cloth cover is secured to the stent by stitching directly through the skirt in the area of reduced thickness resulting from the interrupted channel.

16 Claims, 1 Drawing Sheet

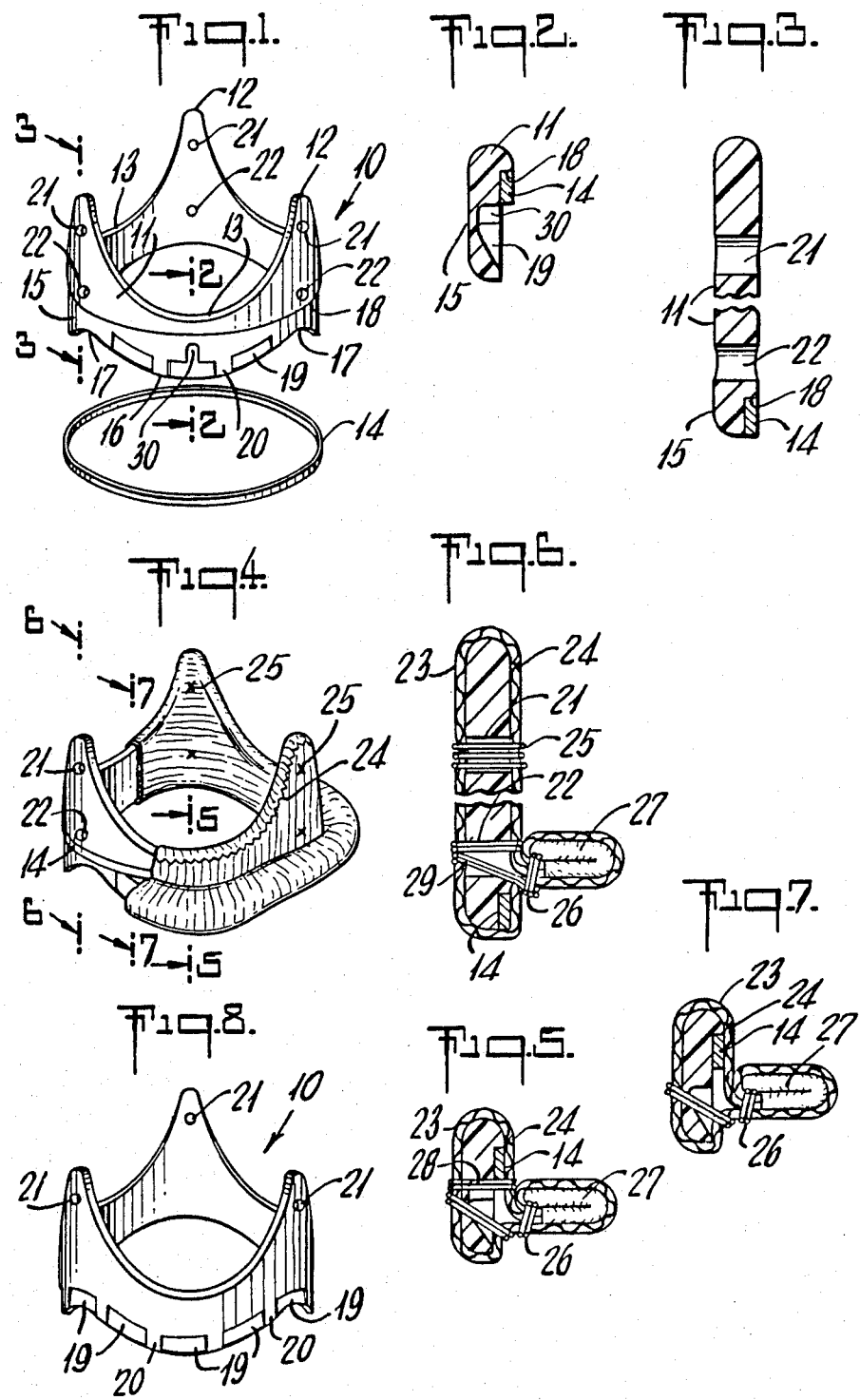

STENT FOR AORTIC HEART VALVE

BACKGROUND OF THE INVENTION

1. Field of the Invention

This invention relates to a polymeric framework or stent for mounting a trileaflet heart valve constructed of natural or synthetic materials, particularly for aortic valve replacement.

2. Description of Prior Art

Frame-mounted, trileaflet heart valves have been widely used for many years as a prosthetic replacement for defective aortic valves in humans. Natural tissue valves have been constructed by mounting gluteraldehyde-fixed porcine heart valves in a suitable framework or stent as described, for example, in U.S. Pat. Nos. 3,570,014, 3,755,823, 3,983,581 and 4,035,849. Similar trileaflet valves have been constructed from autologous and hemologous fascia lata and dura matter, and from heterologous pericardium mounted in a suitable stent as described, for example, in U.S. Pat. Nos. 4,084,268 and 4,172,295.

More recently, efforts have been directed to the development of totally synthetic trileaflet heart valves constructed from tubes and films of biocompatible polymers such as polyurethane. Such valves are also mounted in a stent as described, for example, in U.S. Pat. No. 4,222,126.

Valve stents of the prior art have been constructed of noncorrosive metals such as stainless steel and of plastic such as polypropylene or polyethylene. Plastic stents for porcine valves as described in U.S. Pat. Nos. 3,570,014 and 3,755,823 have an intricate design which requires fabrication by machining from a solid block of polymer at great expense. Plastic stents as described in U.S. Pat. Nos. 3,983,581 and 4,035,849 are of a simpler design and may be formed by injection molding. While such stents are inexpensive, it is somewhat difficult to attach the cloth cover with the recommended method of heat lamination.

It is accordingly an object of the present invention to provide an improved stent for mounting a porcine heart valve.

It is another object of this invention to provide a stent for mounting a trileaflet heart valve wherein the leaflets are constructed of natural or synthetic sheet materials.

It is a further object of this invention to provide a stent for a prosthetic heart valve intended for use in the aortic position.

It is a yet further object of this invention to provide an improved heart valve stent which may be injection-molded and still permit a cloth cover to be attached by stitching.

These and other objects of the present invention will be apparent from the ensuing description and claims.

SUMMARY OF THE INVENTION

This invention is directed to an improved design and construction of a heart valve stent particularly adapted for use in constructing a prosthetic, aortic heart valve utilizing natural or synthetic material. The stent itself is injection-molded of a suitable biocompatible, polymeric material such as polypropylene or polyethylene.

The stent has a cylindrical upper body portion comprising three circumferentially-spaced, axially-extending apical commissure posts or struts interconnected by valleys. The lower portion of the stent forms a skirt comprising three depending arcuate extensions in registry with the valleys of the upper portion. The arcuate extensions are interconnected by arches in registry with the commissure posts of the upper portion. The upper and lower portions of the stent together define a unitary, sculptured, open cylinder having inner and outer surfaces.

Each arcuate extension of the skirt is provided with an edge channel adjacent the lower edge thereof over a major portion of the perimeter of the extension. A side channel centrally disposed in each arcuate extension extends from the edge channel toward the upper body portion of the stent. The edge channels are characterized by having a lower side wall which angles from the base of the channel to the outer edge of the skirt.

The reduced wall thickness of the skirt in the area of the channel is readily pierced by a surgical needle and permits a cloth cover to be attached directly to the stent by stitching through this area. Since the sewing thread actually pierces the stent rather than merely being looped around an arm or strut, or being passed through preexisting holes as in prior art designs, the thread may be precisely placed, and there is no possibility of the cloth cover slipping or being displaced relative to the stent during the stitching procedure.

The lower skirt portion of the stent preferably has a thinner wall and smaller outside diameter than the upper body portion of the stent, thereby creating a circumferential ledge in the outer wall at the line of juncture between the skirt and body portions. The stent may be circumferentially reinforced and made radiopaque if desired with a metal ring fitted about the outside of the skirt adjacent the ledge formed by the upper portion. Preferably, the thickness of the ring conforms to the width of the ledge so that the outside surface of the ring is substantially a continuation of the outside surface of the upper portion of the stent. When the cloth cover and sewing cushion are attached to the stent, the metal ring is fully covered and securely fixed in place.

DRAWINGS

FIG. 1 is a view in perspective of the heart valve stent of the present invention with the metal reinforcing ring shown separately for clarity of illustration.

FIG. 2 is a view in cross-section taken along line 2—2 of FIG. 1.

FIG. 3 is another view in cross-section taken along line 3—3 of FIG. 1.

FIG. 4 is a view in perspective of a covered stent of FIG. 1 including the metal ring and with the cloth cover and sewing cushion shown in partial section.

FIG. 5 is a view in cross-section taken along line 5—5 of FIG. 4.

FIG. 6 is a view in cross-section taken along line 6—6 of FIG. 4 and through a commissure post of the stent.

FIG. 7 is a view in cross-section taken along line 7—7 of FIG. 4 at a point midway between FIGS. 5 and 6.

FIG. 8 is a view in perspective of a heart valve stent of the present invention without the optional metal reinforcing ring.

DESCRIPTION OF INVENTION

Referring now to FIG. 1, there is illustrated a plastic stent 10 according to the present invention, including an optional metal reinforcing ring 14. The stent consists of a cylindrical upper body portion 11 terminating in three axially-extending, commissure posts 12 interconnected by valleys 13 defining a deeply scalloped configuration. The lower skirt portion 15 of the stent is formed by three dependent arcuate extensions 16 interconnected by arches 17. The arcuate extensions are in registry with the valleys of the upper portion while the interconnecting arches are in registry with the commissure posts.

In a preferred embodiment as illustrated in FIG. 1, the outside diameter of the skirt is smaller than the outside diameter of the body portion of the stent thereby creating a circumferential step or ledge 18 in the outer surface of the stent along the line of juncture of the body and skirt portions. Metal ring 14 is sized to fit snugly around the outside of the skirt abutting the upper body portion, and the outer diameter of the metal ring is substantially the same as that of the body portion of the stent so that when in place, the metal ring forms an extension of the outer wall of the body portion of the stent. FIG. 2 is a view in cross section through the stent midway between two commissure posts showing the position of the ring relative to the circumferential ledge of the stent. FIG. 3 is a similar view in cross section through a commissure post.

With further reference to FIG. 1, the skirt is provided with channels 19 traversing the lower edge of the depending arcuate extensions over a major portion of the length thereof. These channels may be continuous over the length of the arcuate extension or interrupted by axially-extending reinforcing ribs 20 as illustrated in FIG. 1. Each arcuate extension includes a centrally disposed side channel 30 extending from the edge channel toward ledge 18, the distance between the blind end of channel 30 and ledge 18 being no greater than the width of ring 14.

Edge channels 19 are configured as best illustrated in the cross-sectional views of FIGS. 2 and 7 where the channel is seen to have a lower side wall angled toward the edge of the arcuate extension. The upper side wall of the channel is substantially perpendicular to the outside surface of the skirt, and the base of the channel is preferably concave as illustrated to form a continuous curve with the side walls. The side channel 30 extends from the base of the edge channel, and the walls of the side channel may be substantially perpendicular to the outside surface of the skirt.

The stent of the present invention is further provided with a first opening 21 in the apical portion of each commissure post, and a second opening 22 in the base of each commissure post proximal to step 18. These openings can be molded, but are preferably drilled and deburred in a separate operation after molding.

The stent of FIG. 1 is prepared for use in mounting a heart valve by adding a cloth cover and a sewing cushion as illustrated in FIGS. 4 through 7. FIG. 4 is a view in perspective of the stent of FIG. 1 with the cloth cover and sewing cushion in place and illustrated in partial section. Cloth cover 23 is constructed of an inner section and an outer section joined at seam 24 which is positioned on the outer surface of the stent to avoid contact with the leaflets of the valve. The cloth cover is secured to the commissure posts by stitching 25 through hole 21 as illustrated in FIG. 6.

The inner section of the cloth cover is brought through the base of the stent and around the bottom of the skirt. Stitching through channels 19 in the skirt secure the cloth cover at the base of the stent body as illustrated in FIGS. 5 and 7. Additional stitching through hole 22 in the body portion of the stent secures the cloth at the base of the commissure post and also secures the metal ring in place as illustrated in FIG. 6. An additional stitch 28 through side channel 30 taken immediately below ring 14 as illustrated in FIG. 5 further secures the ring and tacks the outer cloth cover in place. A similar tacking stitch 29 placed through hole 22 is seen in FIG. 6.

The fabric from the inner cover extends from the skirt to encircle sewing cushion 27 which may be a washer of an elastomeric material such as silicone rubber or a torus formed from a rolled or folded tube of fabric such as a polyester double-knit velour. The edge of the inner cover is folded under and stitched at 26 to secure the sewing ring and edge of the outer cover as illustrated in FIGS. 5 through 7. It will be noted that the sewing cushion follows the contour of the arcuate extensions of the skirt as illustrated in FIG. 4, and the position of the sewing cushion relative to the metal ring varies as illustrated in FIGS. 5 through 7.

The channels in the skirt around the base of the stent are an essential feature of the present invention in regard to both functional and economic considerations. The channels permit the cloth cover to be stitched directly to the stent in a positive and reliable manner. The thickness of the skirt in the area of the base of the channel is sufficiently thin to provide minimal resistance to stitching with a surgical needle, and yet the use of a channel rather than an open slot provides support for the cloth and the stitching. Stitching through the base of the channel assures the stability of the stitch and the cloth covering providing a definite functional advantage. The unique shape of the channel, particularly the angled lower side wall, permits the stent to be injection molded with a simple, one-piece mold. When the stent is removed from the mold, the angled channel side wall acts as a cam surface to deflect the bottom edge of the skirt inward and thereby permit passage of the skirt over the protuberances of the mold which form the channels. The economic advantage of the stent accordingly results from a simplified method of manufacture as compared to machined stents or stents requiring compound molds.

The stents of the present invention are preferably injection-molded of polypropylene or other suitable biocompatible thermoplastic polymeric material. Polypropylene is particularly preferred because it is readily molded, has good strength, and has a moderate degree of flexibility which is desirable to relieve stresses on the stent and the valve material during use. Other suitable materials include Delrin polymer (a polyformaldehyde of greater than 15,000 molecular weight sold by DuPont), Lexan polymer (a polycarbonate), nylon (a hexamethylene diamine-adipic acid polymer) and high density polyethylene. The molded stents are desirably annealed to relieve internal stress and subsequently polished and inspected before covering with cloth. Polypropylene stents may be suitably annealed by heating in an oven at about 90° C. for 20 minutes.

While the preceding description has been directed to a stent which incorporates a metal reinforcing ring, this ring is optional as explained above. If the ring is to be omitted, the stent may be of uniform wall thickness throughout and the step or offset between the upper and lower portion eliminated as illustrated in FIG. 8. In this case, channels 19 preferably extend continuously around the edge of the skirt interrupted only by spaced reinforcing ribs 20. The channels are necessarily deeper due to the greater wall thickness, but the general configuration of the channels is as previously described. Since no ring is present, the side channels previously described are not included in the stent of FIG. 8.

The reinforcing ribs interrupting the channel are preferably equiangularly spaced at 15 to 60° intervals, and preferably at 30° intervals resulting in 12 ribs for the continuous channel illustrated in FIG. 8.

Typical stents for use in the aortic positions in humans have a nominal inside diameter of 16 to 26 mm. When molded of polypropylene, the thickness of the body of the stent is suitably at least about 1.0 mm, and preferably from about 1.0 to 1.5 mm; the skirt is at least about 0.5 mm, and preferably from about 0.5 to 1.5 mm; and the base of the channel is less than about 0.2 mm, and preferably from about 0.1 to 0.15 mm. The step or offset between the upper body of the stent and the skirt is suitably about 0.5 mm wide to accommodate the metal reinforcing ring which is typically 1.0 mm high by 0.5 mm thick. The valve is proportioned approximately according to its nominal size with the maximum axial dimension of the apical, commissure posts of the upper body section being approximately equal to one-half the inside radius of this section, and the minimum axial dimension of the valleys between commissure posts being from about 0.5 to 1.0 mm. The drilled holes in each commissure post are suitably about 0.9 mm in diameter.

The stents of the present invention can be used with good results to mount heart valves of natural or synthetic materials. Natural materials include, without limitation, standard porcine heart valves, modified porcine heart valves as where the leaflet with the septal shelf is replaced with a leaflet from another valve, and natural tissue valves wherein the three cusps of the valve are formed from three separate pieces of pericardial or fascia lata tissue. Synthetic materials include, without limitation, rubberized fabrics, polyurethane film, and one-piece molded polyurethane valves. Rubberized fabric and polyurethane film are utilized in valve construction by forming the three cusps of the valve from separate pieces of material or from a single tubular section. Conventional manufacturing procedures in forming the valve may be followed in all cases.

We claim:

1. A stent for mounting a trileaflet heart valve comprising an upper body portion and a lower skirt portion together defining a unitary, sculptured, open cylinder having inner and outer surfaces, said body portion comprising three circumferentially-spaced, axially-extending, apical commissure posts interconnected by valleys, said skirt portion comprising three depending arcuate extensions in registry with the valleys of said body portion, and a channel traversing the perimeter of said skirt adjacent the lower edge of said arcuate extension, said edge channel being interrupted by a plurality of spaced, axially-oriented reinforcing ribs traversing said channel.

2. The stent of claim 1 wherein said ribs are equiangularly spaced around the circumference of said stent at 15 to 60° intervals.

3. The stent of claim 1 wherein said ribs are equiangularly spaced at 30° intervals.

4. A stent for mounting a trileaflet heart valve comprising a body portion and a skirt portion defining a unitary, sculptured, open cylinder having inner and outer surfaces, said body portion comprising three circumferentially-spaced, axially-extending apical commissure posts interconnected by valleys, said skirt portion comprising three depending arcuate extensions in registry with the valleys of said body portion, the wall thickness of said skirt portion being less then that of said body portion, and the outer surface of said stent including a circumferential step at the juncture of said body and skirt portions corresponding to the difference in wall thickness, and an edge channel traversing the perimeter of said skirt adjacent the edge of said arcuate extensions.

5. The stent of claim 4 wherein the arcuate extensions of said skirt portion are interconnected by arches in registry with the commissure posts of said body portion.

6. The stent of claim 5 wherein said edge channel in each of said arcuate extensions terminates at the arches interconnecting said arcuate extensions.

7. The stent of claim 5 wherein each of said arcuate extensions additionally includes a centrally disposed side channel extending axially toward said circumferential step from said edge channel of said skirt.

8. The stent of claim 4 wherein said edge channel includes a first side wall, a base and an opposing side wall, said first side wall extending at an angle from the edge of said arcuate extension to the base of said channel, said opposing side wall being perpendicular to the surface of said skirt, whereby the width of the channel at its base is substantially less than at the surface of said skirt.

9. The stent of claim 8 wherein the base of said channel is concave and forms a substantially continuous curve with said side walls.

10. The stent of claim 7 wherein said side channel has walls substantially perpendicular to the outer surface of said skirt.

11. The stent of claim 4 additionally including a metal ring circumscribing said skirt portion adjacent said circumferential step in the outer surface of said stent.

12. The stent of claim 6 wherein said edge channel in each of said arcuate extensions is interrupted by reinforcing ribs extending through said channel.

13. The stent of claim 12 having two uniformly-spaced axially-oriented ribs extending through the channel of each of said arcuate extensions.

14. The stent of claim 4 fabricated of polypropylene.

15. The stent of claim 14 wherein the wall thickness of said body portion is from 1.0 to 1.5 mm, and the wall thickness of said skirt portion is about 0.5 mm less than that of said body portion.

16. The stent of claim 14 wherein the wall thickness of the base of said edge channel is less than about 0.2 mm.

* * * * *